United States Patent [19]

Horodysky et al.

[11] 4,255,271
[45] Mar. 10, 1981

[54] PHOSPHORUS-CONTAINING COMPOUNDS AND LUBRICANTS CONTAINING SAME

[75] Inventors: Andrew G. Horodysky, Cherry Hill; Robert M. Gemmill, Jr., Pitman, both of N.J.

[73] Assignee: Mobil Oil Corporation, New York, N.Y.

[21] Appl. No.: 96,114

[22] Filed: Nov. 20, 1979

[51] Int. Cl.$^3$ .............................................. C10M 1/48
[52] U.S. Cl. ............................ 252/46.7; 252/51.5 R; 252/51.5 A; 548/113; 548/216; 548/239
[58] Field of Search ............ 252/32.7 E, 46.7, 51.5 A, 252/51.5 R; 548/113, 216, 239

[56] References Cited

U.S. PATENT DOCUMENTS

| | | | |
|---|---|---|---|
| 2,636,038 | 4/1953 | Brandner | 252/51.5 R X |
| 2,831,858 | 4/1958 | de Benneville et al. | 548/216 X |
| 2,905,644 | 9/1959 | Butter | 252/51.5 R X |
| 2,927,080 | 3/1960 | Westlund, Jr. et al. | 252/46.7 |
| 3,185,647 | 5/1965 | Anderson et al. | 252/46.7 |
| 3,661,922 | 5/1972 | Frump et al. | 548/239 |
| 3,865,740 | 2/1975 | Goldschmidt | 252/46.7 |
| 3,957,746 | 5/1976 | Malec | 252/46.7 |
| 4,028,258 | 6/1977 | Kablaoui et al. | 252/46.7 |
| 4,049,564 | 9/1977 | Ryer et al. | 252/51.5 R X |
| 4,128,558 | 12/1978 | Hendricks et al. | 548/113 X |

*Primary Examiner*—Andrew Metz
*Attorney, Agent, or Firm*—Charles A. Huggett; Michael G. Gilman; Claude E. Setliff

[57] ABSTRACT

Phosphosulfurized hydrocarbyl oxazoline reacted with nitrogen-containing compounds and certain olefins are novel compounds effective for reducing friction and wear when added to a lubricant.

20 Claims, No Drawings

PHOSPHORUS-CONTAINING COMPOUNDS AND LUBRICANTS CONTAINING SAME

BACKGROUND OF THE INVENTION

1. Field of the Invention

The invention is concerned with a novel group of compounds and their use in lubricants as friction reducers, antioxidants and antiwear corrosivity reducers (e.g. copper corrosion reducers).

2. Discussion of the Prior Art

It is known that sliding or rubbing metal or other solid surfaces are subject to wear under conditions of extreme pressure. Wearing is particularly acute in modern engines in which high temperatures and contact pressures are prevalent. Under such conditions, severe erosion of metal surfaces can take place even with present generation lubricants unless a load carrying or antiwear additive is present therein.

Friction is also a problem any time two surfaces are in sliding or rubbing contact. It is of especial significance in an internal combustion engine and related power train components, because loss of a substantial amount of the theoretical mileage possible from a gallon of fuel is traceable directly to friction.

With respect to the novel compounds of this invention, they are made by (1) forming an oxazoline from one mole of monocarboxylic acid and one mole of a hydroxyamine (e.g. 2-amino-2-(hydroxymethyl)-1,3-propanediol, also known as tris(hydroxymethyl)aminomethane, (2) reacting this with phosphorus sulfide and (3) forming a nitrogen-containing compound, an activated olefin or an epoxide derivative. The reaction to prepare the oxazoline is known, as is the reaction of the two hydroxyl groups thereof with P$_2$S$_5$ to form the ashless derivatives. However, no art is known that teaches or suggests the novel compounds or their use as lubricant additives.

SUMMARY OF THE INVENTION

In accordance with the invention there is provided a compound prepared by reacting one molar amount of a carboxylic acid of the formula

R—COOH wherein R is a hydrocarbyl containing from 9 to 49 carbon atoms with one molar amount of tris(hydroxymethyl)aminomethane, reacting the resulting product with a phosphorus polysulfide, particularly phosphorus pentasulfide, and reacting the product thus obtained with a member of the group consisting of a nitrogen-containing compound, an epoxide and an activated olefin. "Hydrocarbyl" is preferably alkyl, including nonyl, decyl, dodecyl, tetradecyl, octadecyl, eicosyl, and the like, or alkenyl. It can also be aryl, in which the aryl nucleus has 6 to 14 carbon atoms. "Molar amount" includes more or less than one mole.

The invention also provides a lubricant composition comprising a lubricant and a friction reducing or antiwear amount of the product. It is further contemplated that the product will aid in the reduction of fuel consumption in an internal combustion engine.

DESCRIPTION OF SPECIFIC EMBODIMENTS

As has been mentioned hereinabove, the compounds of this invention can be made by reacting a monocarboxylic acid with a hydroxyamine, reacting the product thus formed with a phosphorus sulfide and then with the specified compound. The following reactions illustrate what we believe to be the major product from the reaction.

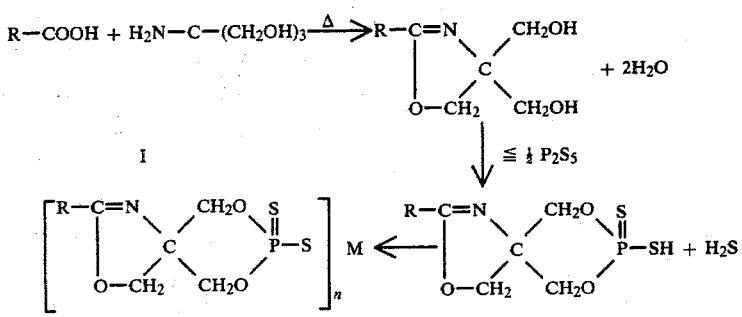

where R and M are as defined above, M is a nitrogen-containing compound, an epoxide or an activated olefin and n is equal to the valence of M. However, the reaction with P$_2$S$_5$ probably produces a complex mixture of products having structures like the following:

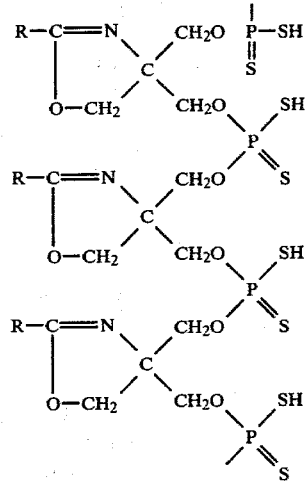

When this and other possible compounds are reacted with the specified compound, the mixture becomes even more complex. Since the product is a complex mixture, it will be claimed as a reaction product, although it is believed to contain a predominant amount of compound I.

The carboxylic acid, as indicated, may have from 10 to 50 carbon atoms, including the carboxyl carbon atom. These include the saturated decanoic (capric), dodecanoic (lauric), tetradecanoic (myristic), octadecanoic (stearyl), eicosanoic (arachidic) acids and the like, as well as the unsaturated acids, including particularly oleic acid.

The first reaction, i.e. between the monocarboxylic acid and the amine, can be carried out at from about 80° C. to about 250° C., preferably from about 120° C. to about 190° C. The temperature chosen will depend for the most part on the particular reactants and on whether or not a solvent is used. In carrying out this reaction, it is essential that quantities of reactants be chosen such that at least two hydroxyl groups remain on most of the oxazoline molecules for the reaction with phosphorus sulfide. For example, in the reaction illustrated, one mole of the acid and one mole of the amine are required. An excess of acid in this case would possibly lead to the formation of some monoester oxazoline in addition to the named oxazolines.

In carrying out the reaction to form the phosphorodithioic acid, stoichiometric amounts of $P_2S_5$ may be used. Generally, however, a slight excess of $P_2S_5$, not exceeding about 10 to 20% by weight is preferred. Of course, this will be a matter of choice, the choice being governed by several factors, among them economics.

The final reaction, i.e. with the nitrogen-containing compound, activated olefin or epoxide, can be carried out at from about 50° C. to about 125° C., preferably from about 70° C. to about 100° C. Again, stoichiometric amounts of reagents are used, or, if desired, an excess of from about 1 to 30% can be employed. A larger excess of some of the more volatile olefins can be used and such excess can then be removed by vacuum distillation.

While atmospheric pressure is generally preferred, the reaction can be advantageously run at from about 1 to about 3 atmospheres. Furthermore, where conditions warrant it, a solvent may be used. In general, any relatively non-polar, unreactive solvent can be used, including toluene, xylene and 1,4-dioxane.

The times for the reactions are not critical. Thus, any phase of the process can be carried out in from 1 to 8 hours.

The nitrogen-containing compound used includes a primary, secondary or tertiary straight, branched-chain or cyclic amine containing 10 or more carbon atoms, preferably, from 10 to 100 carbon atoms. These further include saturated and unsaturated simple amines, as for example, decyl-, dodecyl- and tridecylamine, tetradecyl-, ditetradecyl- and tritetradecylamine, octadecyl-, dioctadecyl- and trioctadecylamine, and the like as well as oleyl amine.

They also include polyalkyleneamines such as the polyalkylene polyamine of the formula NH$_2$(RNH)$_n$RNH$_2$ wherein R is an alkylene group having from 1 to 5 carbon atoms and n is from 0 to 10. Suitable polyamines may be methylenediamine, ethylenediamine, diethylenetriamine, triethylenetetramine, tetraethylenepentamine, hexaethyleneheptamine and the like. The cyclic amines may be illustrated by mentioning cyclohexylamine and dicyclohexylamine.

The amines may also be aromatic amines wherein the aromatic portion contains 6 to 14 carbon atoms.

The activated olefins contemplated include the sulfurized olefins and dienes, the latter having from 10 to 120 carbon atoms. Such compounds also contemplate the use of unsaturated aldehydes of the formula

RCH=CHCHO unsaturated vinyl esters of the formula

RCH=CHCOOR' unsaturated vinyl ethers of the formula

RCH=CHOR' unsaturated ketones of the formula $$RCH=CH-\overset{O}{\underset{\|}{C}}-R'$$

and acrylonitrile. In these formulas, R and R' may be the same or different and contain from 10 to 100 carbon atoms. R and R' may also be hydrogen.

A further class of compounds that may be employed as reactants are the sulfurized olefins as described in U.S. Pat. No. 3,703,504, the disclosure of which is incorporated herein by reference.

As is disclosed, one of the olefin reactants is a sulfurized olefin. These are generally described in U.S. Pat. No. 3,703,504, the entirety of which is incorporated herein by reference. This class of reactant, however, is not limited thereto.

Sulfurized olefins made by variations of these processes or by other processes known to the art which contain sulfur may be employed in the invention. Dimethallyl sulfides such as:

$$\underset{CH_2=\overset{CH_3}{\underset{|}{C}}-CH_2-S_x-CH_2-\overset{CH_3}{\underset{|}{C}}=CH_2}{}$$

where x=1, 2, 3, 4 etc.
which can be formed by the reaction of methallyl chloride with an alkali metal monosulfide, alkali metal disulfide or alkali metal polysulfide, may be employed in this invention. Other high sulfur content sulfurized hydrocarbons may likewise be employed in this invention.

Generally speaking, the sulfurized olefins are obtained via a process which comprises sulfohalogenating an olefin with a sulfur halide in the presence of a catalytic quantity (i.e. 0.2–10 wt. % based on the halide) of a lower aliphatic alcohol having up to about 10 carbon atoms (e.g., methanol, ethanol, propanol, i-propanol, butanol, i-butanol, etc.) to form a sulfohalogenated organic intermediate, and thereafter sulfurizing and dehalogenting said intermediate in the presence of a substantial quantity of lower aliphatic alcohol, e.g., form a sulfohalogenated organic intermediate, and thereafter sulfurizing and dehalogenating said intermediate in the presence of a substantial quantity of lower aliphatic alcohol, e.g., from 10 to about 50% by weight of the adduct by treatment with an aqueous alkali metal sulfide solution, or an aqueous alkali metal monosulfide solution (which can be derived, for example, from a spent aqueous alkali metal hydroxide effluent from hydrocarbon purification) having a substantial combined sulfur content, thus producing an organic sulfide of high combined sulfur content.

A wide variety of olefin substances may be charged to the initial sulfochlorination reaction, including olefins having a single terminal or internal double bond. The olefinic substances usually contain from about 2 to 8 or more carbon atoms per molecule and may be either straight, branched chain or cyclic. These may be exemplified by ethylene, propylene, butene-1, cis- and trans-butene-2, isobutylene, diisobutylene, triisobutylene, the pentenes, cylcopentene, the hexenes, cyclohexene, the octenes and decene-1. Isobutylene is the preferred olefinic reactant. In general, $C_{3-6}$ olefins or mixtures thereof are desirable for preparing sulfurized products for use herein as lube oil additives. The combined sulfur content of the product decreases with increasing carbon content while its miscibility with oil is lower for propylene and ethylene derivatives.

The other reactant in the first stage is preferably sulfur monochloride ($S_2Cl_2$), but other similar compounds, such as sulfur dichloride and $S_3Cl_2$ and the corresponding sulfur bromides may be employed in an amount which will provide a quantity of sulfur corresponding to desirable reactant ratios for sulfur monochloride. The molar ratio of olefin to sulfur monohalide may range from about 1:1 up to 1.7:1 or more. In the case of isobutylene and sulfur monochloride, the optimum ratio appears to be between about 1.55:1 and 1:60:1.

The initial reaction can be catalyzed with a lower aliphatic alcohol containing from 1 to 4 carbon atoms, as exemplified by methanol, ethanol, propanol and isopropanol. Of these, methanol and ethanol are usually preferred. The spent aqueous alkali metal hydroxide effluent as mentioned hereinabove is derived primarily from spent organic caustic liquors issuing from integrated refinery processes.

The sulfurized olefins produced by the above-described process have very high sulfur content, i.e. more than about 35% by weight (typically about 46–48% of combined sulfur) and are substantially devoid of free sulfur. Other sulfurized olefins made by variations of this process or by other processes known to the art which have a sulfur content of about 30% and above may also be employed in this invention.

The reaction is usually carried out at temperatures of from about 75° to 120° C., preferably from 80°–110° C., under atmospheric pressure (although higher pressures may be used if desired) for periods of up to about 16–20 hours, e.g., preferably from about 1 to about 10 hours or more. The reaction mixture is heated with agitation to the desired temperature. The reaction may also be carried out in the absence of any added solvent or it may be carried out in a non-reactive solvent such as pentane, hexane, heptane, cyclohexane, benzene, toluene and the like, or a refined petroleum oil may be employed therefor. Further, the reaction may be carried out in a more polar solvent such as ethanol, isopropanol, or one of the butanols. In some cases, isopropanol is preferred.

Of particular significance, in accordance with the present invention, is the ability to improve the resistance to oxidation and corrosion of oleaginous materials such as lubricating media which may comprise liquid oils, in the form of either a mineral oil or a synthetic oil, or in the form of a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F., and preferably, from about 50 to about 250 SSU at 210° F. These oils may have viscosity indexes ranging to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis (p-phenoxy phenyl) ether, phenoxy phenylethers.

It is to be understood, however, that the compositions contemplated herein can also contain other materials. For example, corrosion inhibitors, extreme pressure agents, viscosity index improvers, co-antioxidants, anti-wear agents and the like can be used. These materials do not detract from the value of the compositions of this invention, rather the materials serve to impart their customary properties to the particular compositions in which they are incorporated.

Mineral oil heat exchange fluids particularly contemplated in accordance with the present invention have the following characteristics: high thermal stability, high initial boiling point, low viscosity, high heat-carrying ability and low corrosion tendency.

Further, the transmission fluids of consequence to the present invention are blends of highly refined petroleum base oils combined with VI improvers, detergents, defoamants and special additives to provide controlled-friction or lubricity characteristics. Varied transmission design concepts have led to the need for fluids with markedly different frictional characteristics, so that a single fluid cannot satisfy all requirements. The fluids intended for use in passenger car and light-duty truck automatic transmissions are defined in the ASTM Research Report D-2: RR 1005 on "Automatic Transmission Fluid/Power Transmission Fluid Property and Performance Definitions" Specifications for low-temperature and aircraft fluids are defined in U.S. Government Specification MIL-H-5606A.

In addition, the oxidation and corrosion resistance of functional fluids such as hydraulic fluids can be improved by the adducts of the present invention.

In general, the preformed adducts of the present invention may be employed in any amount which is effective for imparting the desired degree of friction reduction or antiwear activity. In many applications, however, the adduct is effectively employed in amounts from about 0.1% to about 10% by weight, and preferably from about 1 to about 5% of the total weight of the composition.

The following Examples will present illustrations of the invention. They are illustrative only, and are not meant to limit the invention.

EXAMPLE 1

A reactor fitted with a nitrogen inlet, stirrer, thermometer, Dean-Stark water trap and condenser was used for the reaction.

Oleic acid (1.0 mole, 282.0 grams), 2-amino-2-(hydroxymethyl)-1,3-propanediol (1.0 mole, 121.0 grams) and 200 ml. of xylene were charged to the reactor.

The reaction mixture was heated, using a nitrogen purge and rapid stirring, to a maximum temperature of 162° C. for 13 hours. Water evolved over the temperature range of 125°–162° C. A total of 35 ml. of water (theory=36 ml.) was collected. The product was di(hydroxymethyl)heptadecenyl oxazoline. Toluene (300 ml.) was added to the product and $P_2S_5$ (0.55 mole, 122.1 grams) was added slowly over a period of two hours at a temperature of 70°–82° C. The reaction was run for a total of 12 hours over a temperature range of 70°–115° C. The reaction product was a clear, amber fluid. The toluene and xylene were removed by vacuum distillation. The product was a clear, amber, oil soluble solid at room temperature. A synthetic hydrocarbon diluent oil (502 grams) was added to give a product (approx. 48–49% active ingredient) which was a clear, amber, low-melting, oil soluble gel.

EXAMPLE 2

The reaction was performed in a reactor fitted with a stirrer, thermometer and condenser.

The phosphosulfurized di(hydroxymethyl)heptadecenyl oxazoline (49% active) of Example 1 (0.104 mole, 100.0 grams), oleyl amine (0.110 mole, 29.4 grams) and 200 ml. toluene were charged to the reactor. The reaction mixture was stirred for 7 hours at 22°–85° C. The toluene was removed by vacuum distillation and the product vacuum filtered through diatomaceous earth filter aid. The product was a clear, amber fluid containing 61% active amine salt.

EXAMPLE 3

The reaction was performed in a reactor fitted with a stirrer, thermometer and condenser.

The phosphosulfurized di(hydroxymethyl)heptadecenyl oxazoline (49% active) of Example 1 (0.104 mole, 100.0 grams), N-oleyl-1,3-propylenediamine (0.054 mole, 17.5 grams) and 200 ml. of toluene were charged to the reactor. The reaction mixture was stirred for four hours at 25°–71° C. The toluene was removed by vacuum distillation and the product vacuum filtered through diatomaceous filter aid. The product was a clear, amber fluid containing 57% active amine salt.

EXAMPLE 4

Approximately 93 grams of the phosphosulfurized di(hydroxymethyl)heptadecenyl oxazoline product of Example 1 was charged to a reactor fitted with a stirrer, thermometer, condenser, and addition funnel. Benzene (88 grams) was added and the reactor contents heated to 80° C. with agitation. Over a period of one hour, 10 grams of butyl vinyl ether was slowly added. The reactor was held for an additional 3 hours at 80°–85° C. The excess reactants and solvent were removed by vacuum distillation at 80°–85° C. The product was an orange liquid.

EXAMPLE 5

Approximately 100 grams of sulfurized isobutylene prepared in accordance with Example 1 of U.S. Pat. No. 3,703,504 was charged to a 500 ml. glass reactor fitted with a stirrer, thermometer, condenser and addition funnel. Approximately 75 grams of the phosphosulfurized di(hydroxymethyl)heptadecenyl oxazoline product of Example 1 was added to the reaction mixture and heated with agitation at 100° C. for four hours. The reactor was then heated to 120°–130° C. for four additional hours and then cooled. The product was an orange viscous liquid.

EVALUATION OF THE COMPOUNDS

The compounds were evaluated in a low velocity friction apparatus (LVFA) in a fully formulated 5W-20 synthetic oil containing an additive package including antioxidant, dispersant and detergent. The test compound was 2–4% of the total weight of oil.

Description

The Low Velocity Friction Apparatus (LVFA) is used to measure the coefficient of friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam-motor arrangement.

Procedure

The rubbing surfaces and 12–13 ml. of test lubricants are placed on the LVFA. A 240 psi load is applied, and the sliding speed is maintained at 40 fpm at ambient temperature for a few minutes. A plot of coefficients of friction ($U_k$) vs. speed were taken at 240, 300, 400, and 500 psi. Freshly polished steel specimens are used for each run. The surface of the steel is parallel ground to 4 to 8 microinches. The results in Table 1 refer to percent reduction in friction compared to the unmodified oil. That is, the formulation mentioned above was tested without the compound of this invention and this became the basis for comparison. The results were obtained at 250° F. and 500 psi.

TABLE 1

EVALUATION OF FRICTION REDUCING CHARACTERISTICS

| Compound | Additive Conc. Wt. % in Test Oil | % Change in of Friction 5 ft./min. | Coefficient at 30 ft./min. |
|---|---|---|---|
| Test Oil | 0 | 0 | 0 |
| Example 2 | 4 | 29 | 20 |
| Example 3 | 4 | 21 | 17 |
| Example 5 | 2 | 10 | 15 |

Representative samples of the above prepared compositions were also evaluated for antioxidant properties with a catalytic oxidation test. A sample of the base lubricant was placed in an oven at 325° F. Present in the sample were the following metals either known to catalyze organic oxidation or commonly used materials of construction:
  a. 15.6 sq. in. of sand-blasted iron wire
  b. 0.78 sq. in. of polished copper wire
  c. 0.87 sq. in. of polished aluminum wire
  d. 0.167 sq. in. of polished lead surface
Dry air was passed through the sample at a rate of about 5 liters per hour for 40 hours. Table 2 shows the data.

TABLE 2

Catalytic Oxidation Test 325° F. 40 Hours

| | Additive Conc. Wt. % in Base Oil | Lead Loss, mg. | Percent Incr. in Visc. of Oxidized Oil KV @ 100° C. | Neutralization Number |
|---|---|---|---|---|
| Base Oil 200" Solvent Paraffinic Neutral Lubricating Oil | 0 | 0.4 | 27 | 2.21 |
| Example 4 | 1 | 0.0 | 19 | — |
|  | 3 | 0.0 | 17 | — |
| Example 5 | 1 | 0.0 | 10 | — |
|  | 3 | 0.0 | 8 | 1.01 |

We claim:
1. A compound prepared by reacting one molar amount of a carboxylic acid of the formula

R—COOH wherein R is a hydrocarbyl containing from 9 to 49 carbon atoms with one molar amount of tris(hydroxymethyl)aminomethane, reacting the resulting product with a phosphorus polysulfide, and reacting the product thus obtained with a member of the group consisting of a nitrogen-containing compound selected from the group consisting of (1) primary, secondary and tertiary amines containing 10 or more carbon atoms and (2) a polyalkyleneamine, an epoxide and an activated olefin selected from the group consisting of dienes, unsaturated aldehydes, vinylic esters, vinylic ethers, vinylic ketones, acrylonitrile and sulfurized olefins.

2. The compound of claim 1 wherein R is a heptadecenyl group.
3. The compound of claim 1 wherein the polyalkylene amine is a polyalkyleneamine of the formula $NH_2(RNH)_nRNH_2$ wherein R is an alkylene group having 1 to 5 carbon atoms and n is from 0 to 10.
4. The compound of claim 1 wherein the nitrogen-containing compound is oleyl amine.
5. The compound of claim 1 wherein the nitrogen-containing compound is N-oleyl-1,3-propylene diamine.
6. The compound of claim 1 wherein the activated olefin is a sulfurized olefin.
7. The compound of claim 6 wherein the sulfurized olefin is sulfurized isobutylene.
8. The compound of claim 1 wherein the activated olefin is butyl vinyl ether.
9. A lubricant composition comprising a major proportion of a lubricant and a friction reducing amount of a compound prepared by reacting one molar amount of a carboxylic acid of the formula

R—COOH wherein R is a hydrocarbyl containing from 9 to 49 carbon atoms with one molar amount of tris(hydroxymethyl)aminomethane, reacting the resulting product with a phosphorus polysulfide, and reacting the product thus obtained with a member of the group consisting of a nitrogen-containing compound selected from the group consisting of (1) primary, secondary and tertiary amines containing 10 or more carbon atoms and (2) a polyalkyleneamine, an epoxide and an activated olefin selected from the group consisting of dienes, unsaturated aldehydes, vinylic esters, vinylic ethers, vinylic ketones, acrylonitrile and sulfurized olefins.

10. The composition of claim 9 wherein R is a heptadecenyl group.
11. The composition of claim 9 wherein the polyalkylene amine is a polyalkyleneamine of the formula $NH_2(RNH)_nRNH_2$ wherein R is an alkylene group having 1 to 5 carbon atoms and n is from 0 to 10.
12. The composition of claim 9 wherein the nitrogen-containing compound is oleyl amine.
13. The composition of claim 9 wherein the nitrogen-containing compound is N-oleyl-1,3-propylene diamine.
14. The composition of claim 9 wherein the activated olefin is a sulfurized olefin.
15. The composition of claim 14 wherein the sulfurized olefin is sulfurized isobutylene.
16. The composition of claim 9 wherein the activated olefin is butyl vinyl ether.
17. A method of reducing the fuel comsumption of an internal combustion engine by lubricating said engine with a lubricating oil composition comprising a major proportion of a lubricating oil and a friction reducing amount of a compound prepared by reacting one molar amount of a carboxylic acid of the formula

R—COOH wherein R is a hydrocarbyl containing from 9 to 49 carbon atoms with one molar amount of tris(hydroxymethyl)aminomethane, reacting the resulting product with a phosphorus polysulfide, and reacting the product thus obtained with a member of the group consisting of a nitrogen-containing compound selected from the group consisting of (1) primary, secondary and tertiary amines containing 10 or more carbon atoms and (2) a polyalkyleneamine, an epoxide and an activated olefin selected from the group consisting of dienes, unsaturated aldehydes, vinylic esters, vinylic ethers, vinylic ketones, acrylonitrile and sulfurized olefins.

18. The compound of claim 1 wherein the phosphorus polysulfide is phosphorus pentasulfide.

19. The composition of claim 9 wherein in said compound the phosphorus polysulfide is phosphorus pentasulfide.

20. The method of claim 17 wherein in said compound the phosphorus polysulfide is phosphorus pentasulfide.

* * * * *